United States Patent [19]

Nozaki

[11] Patent Number: 5,399,647
[45] Date of Patent: Mar. 21, 1995

[54] PHOTORESIST COMPOSITION OF 1-(1'-CYANOETHENYL)ADAMANTANE

[75] Inventor: Koji Nozaki, Kawasaki, Japan

[73] Assignee: Fujitsu Limited, Kawasaki, Japan

[21] Appl. No.: 275,360

[22] Filed: Jul. 15, 1994

Related U.S. Application Data

[62] Division of Ser. No. 74,755, Jun. 10, 1993, Pat. No. 5,342,735.

[30] Foreign Application Priority Data

Jun. 10, 1992 [JP] Japan ................................ 4-150645
Jun. 30, 1992 [JP] Japan ................................ 4-173129

[51] Int. Cl.⁶ ............................................. G03C 1/73
[52] U.S. Cl. ................................... 526/297; 430/270; 526/282; 585/21; 585/317
[58] Field of Search ................... 526/297, 282; 585/21, 585/317; 430/270

[56] References Cited

U.S. PATENT DOCUMENTS 3,457,318  7/1969  Capaldi ........................... 585/317
5,053,568 10/1991  Chen ............................... 585/21

FOREIGN PATENT DOCUMENTS 1262601  3/1968  Germany .

*Primary Examiner*—Fred Zitomer
*Attorney, Agent, or Firm*—Staas & Halsey

[57] ABSTRACT

New copolymers are disclosed which are copolymers of 1-(1'-cyanoethenyl)adamantane or 2-norbornene-2-carbonitrile monomer with an acrylate or methacrylate monomer. Resist compositions are also disclosed which comprise one of the disclosed new copolymers and an acid generator. The resist compositions advantageously form thinner resist films on substrates and, on the exposure to light having a short wavelength, such as KrF and ArF excimer laser light, provide finer resist pattern required in the production of advanced, highly integrated semiconductor devices. Novel 1-(1'-cyanoethenyl)adamantane is also disclosed.

5 Claims, No Drawings

PHOTORESIST COMPOSITION OF 1-(1'-CYANOETHENYL)ADAMANTANE

This application is a division of application Ser. No. 08/074,755, filed Jun. 10, 1993, now U.S. Pat. No. 5,342,735.

BACKGROUND OF THE INVENTION

1. Field of the Invention

The present invention relates to a new copolymer of an aliphatic polycyclic monomer having an alpha, beta-unsaturated nitrile with a certain copolymerizable monomer, and particularly, to copolymers of 1-(1'-cyanoethenyl)adamantane or 2-norbornene-2-carbonitrile with an acrylate or methacrylate derivative. These copolymers would be used as functional polymer materials for various electrical, optical, and medical uses.

The invention also relates to resist compositions of the chemical amplification type comprising the copolymer of the invention and a photo acid generator. These compositions are advantageously used as resist materials particularly in the production of highly integrated semiconductor devices.

The invention further relates to 1-(1'-cyanoethenyl)adamantane which is a novel compound and is used as the starting material for the copolymer. In addition, this novel compound may be used as a starting material for synthesis of various organic compounds and polymers.

2. Description of the Related Art

Certain compounds having an adamantane skeleton and a substituent containing a polymerizable double bond are known. These compounds include, e.g., 1-vinyladamantane and 1-isopropenyladamantane. The only known polymer materials obtained from such known adamantane compounds are homopolymers produced using a cationic catalyst such as aluminum bromide (Miljenko Zuanic et al., J.Polym. Sci., Polym. Lett. Ed., 19,387 (1981)), and radical copolymers of such an adamantane compound with maleic anhydride or maleimide having a double bond of very low electron density.

For unsaturated compounds having a norbornene skeleton, many compounds are known, including, e.g., norbornylene and 5-vinyl-2-norbornene. Also, many polymers are known which use such known norbornene compounds as a main moiety. However, copolymers of 2-norbornene-2-carbonitrile and an acrylate or methacrylate derivative according to the present invention are not known. Further, with 1,2-substituted olefinic compounds such as norbornylene, the only polymers which are known are obtained by ring opening polymerization through a Lewis acid catalyst such as titanium tetrachloride, and which are copolymers obtained by radical polymerization of such a compound with maleic anhydride or maleimide having a double bond of very low electron density.

Thus, both prior adamantane compounds and norbornene compounds can provide limited copolymers such as those delineated above, but cannot provide other copolymers such as those obtained by polymerization between an adamantane or norbornene compound and a monomer having wider uses such as an acrylic or methacrylic compound. The prior adamantane and norbornene compounds therefore make it difficult to modify copolymerized materials so as to attain desired properties.

For example, when the prior copolymers are applied to photoresist materials used for a photolithographic process in the manufacture of semiconductor devices, the copolymers have disadvantages and are difficult to process into a thin film due to the hardness of the copolymer, and thus prevent the production of a fine resist pattern due to their high absorption of far ultraviolet rays. Advanced photolithographic processes used in the semiconductor device manufacture particularly require photoresist materials showing high transparency to shorter wavelength radiation, such as far ultraviolet rays, so as to allow the production of more and more highly integrated devices. It would therefore be beneficial to the art of manufacture of highly integrated semiconductor devices, to provide a resist material having excellent properties from which finer resist films can be obtained.

To the inventor's knowledge, the adamantane compound of 1-(1'-cyanoethenyl)adamantane, which may be used a starting material for the copolymers of the invention, was not known prior to the present invention.

SUMMARY OF THE INVENTION

It is an object of the invention to provide novel copolymers of 1-(1'-cyanoethenyl)adamantane or 2-norbornene-2-carbonitrile, and an acrylic or methacrylic derivative monomer, which would exhibit unique properties and be useful in various applications such as in electrical, optical, and medical uses.

It is another object of the invention to provide novel resist compositions which use the copolymer of the invention as a base resin, and which allow the formation of a finer resist pattern.

It is also an object of the invention to provide a novel adamantane compound, 1-(1'-cyanoethenyl)adamantane, from which one of the copolymers of the invention is obtained.

In an aspect of the invention, there is provided a copolymer of 1-(1'-cyanoethenyl)adamantane with an acrylate or methacrylate derivative represented by the following formula:

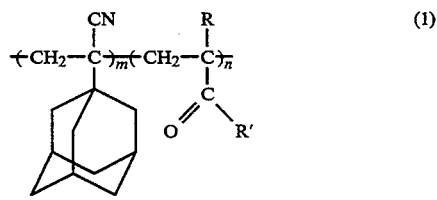

wherein R is hydrogen or methyl group;

R' is hydroxyl group, halogen, such as chlorine, an alkoxyl group, or a heteroatom-containing alkoxyl group; and m and n are integers greater than zero.

In another aspect of the invention, there is provided a copolymer of 2-norbornene-2-carbonitrile with an acrylate or methacrylate derivative having the following formula:

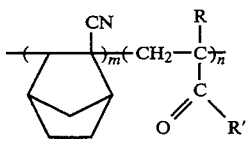 (2)

wherein R is hydrogen or methyl group;

R' is hydroxyl group, halogen, such as chlorine, an alkoxyl group, or a heteroatom-containing alkoxyl group; and m and n are integers greater than zero.

According to the invention, there is also provided a resist composition which comprises a copolymer of 1-(1'-cyanoethenyl)adamantane with an acrylate or methacrylate derivative having the following formula:

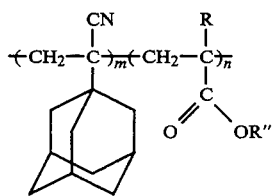

wherein R" is a tert-butyl group or tetrahydropyranyl group, and R, m and n have the same meanings as those described above; and an acid generator.

Also according to the invention, there is provided a resist composition which comprises a copolymer of 2-norbornene-2-carbonitrile with an acrylate or methacrylate derivative having the following formula:

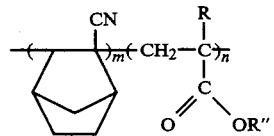

wherein R" is a tert-butyl group or tetrahydropyranyl group, and R, m and n have the same meanings as those described above; and an acid generator.

Both of the copolymers used in the resist compositions of the invention have an average molecular weight of 2,000 to 1,000,000, and preferably 5,000 to 100,000. The ratio of m to n in the copolymer is preferably 30:70 to 70:30, more preferably 40:60 to 60:40, and most preferably about 50:50. In the resist compositions of the invention, the acid generator is present in an amount of 1 to 50% by weight, and preferably 5 to 20% by weight, based on the weight of the copolymer used in the composition.

The invention further provides 1-(1'-cyanoethenyl)adamantane as an novel compound represented by the following formula:

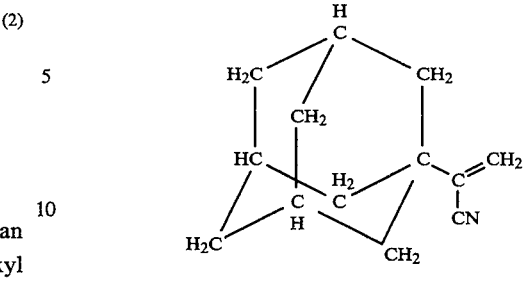

This compound can easily be copolymerized with other monomer such as an acrylate or methacrylate derivative, to thereby provide various novel copolymers having adamantyl groups bonded directly to the main chain. This novel adamantane compound could be used as a starting material for synthesis of various organic compounds and polymers. For example, since it is known that an adamantane compound has a carcinostatic property, the inventive compound may be used in the pharmaceutical art.

DETAILED DESCRIPTION OF THE INVENTION

The copolymer represented by the above formula (1) is prepared using 1-(1'-cyanoethenyl)adamantane and an acrylate or methacrylate derivative as starting materials. Also, the copolymer represented by formula (2) is prepared using 2-norbornene-2-carbonitrile and an acrylate or methacrylate derivative as starting materials. The starting materials may be radical-polymerized using an azo radical initiator such as azoisobutyronitrite, or may be anionic-polymerized using an alkyl lithium compound such as n-butyl lithium, or a Grignard reagent such as phenyl magnesium bromide, in an aromatic hydrocarbon solvent such as benzene or toluene and under an inert atmosphere of, e.g., nitrogen or argon. Furthermore, the starting materials may be anionic-polymerized using a metal alkoxide reagent such as potassium tert-butoxide, in tetrahydrofuran and an atmosphere of inert gas such as nitrogen or argon.

The compounds which are copolymerized with 1-(1'-cyanoethenyl)adamantane or 2-norbornene-2-carbonitrile are not limited to acrylate and methacrylate derivatives, as long as they are monomers having Q and e values similar to those of the acrylate or methacrylate compounds. The processes for copolymerization are also not limited, although an anionic copolymerization which uses a metal alkoxide reagent in tetrahydrofuran and an atmosphere of inert gas such as nitrogen or argon is preferred.

The copolymers of the invention would be useful in various applications such as in electrical, optical, and medical uses.

The copolymers of the invention are particularly useful for base resins in resist compositions used to form finer patterns in the lithographic processes during the manufacture of semiconductor devices. Thus, the invention provides novel types of resist materials comprising copolymers having the following formula:

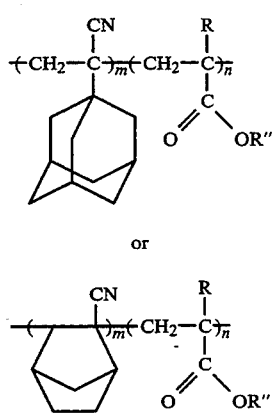

or wherein R is hydrogen or methyl group;

R" is tert-butyl group or tetrahydropyranyl group; and m and n are integer greater then zero, and the ratio of m to n is preferably 30:70 to 70:30, more preferably 40:60 to 60:40, and most preferably about 50:50; the composition further containing an acid generator. The copolymer in the resist composition has an average molecular weight of 2,000 to 1,000,000, and preferably 5,000 to 100,000. The acid generator is present in the composition, in an amount of 1 to 50% by weight, and preferably 5 to 20% by weight, based on the weight of the copolymer in the composition.

The resist composition of the invention, which utilizes an acid generator, is a type of resist material known as chemically amplified resist. In such a chemically amplified resist, the acid generator liberates acid by the exposure to, e.g., light, and the generated acids then catalize the deprotection of the acid labile ester in the copolymer by which the copolymer becomes soluble in an alkaline solution. The deprotection of the acid labile ester also generates acids which in turn participate in the further reaction.

In the resist compositions of the invention, copolymers are preferentially used which have an R" group capable of being easily deprotectable from the ester under the operation of acid, and simultaneously generates additional acid. The ester group removed from the copolymer should be stable. R" groups preferably used in the composition include tert-butyl and tetrahydropyranyl groups. This preference is based on the nature of these groups to satisfy the above-mentioned requirements and the availability thereof.

Conventional phenolic novolak based photoresists have disadvantages of providing inferior resist patterns and low sensitivity when irradiated with short wavelength rays such as far ultraviolet rays, because these resists strongly absorb short wavelength rays. For example, the resists are opaque to ArF excimer laser light having a wavelength of 193 nanometers, and exhibit low transparency even to KrF excimer laser light of a wavelength of 248 nanometers. In contrast, the inventive copolymers have a high transmittance of about 90% for light of a wavelength of 248 nanometers, and a transmittance of about 50% for light of 193 nanometers. Thus, the resist compositions comprising the copolymer according to the invention are capable of being exposed not only to KrF excimer laser but also ArF excimer laser of shorter wavelength, for the desired resist pattern formation, in combination with an appropriate photo acid generator.

The inventive resist compositions of the chemical amplification type have high sensitivity because the acid liberated from the acid generator at the exposed regions in a resist film causes the chain reaction of the deprotection of acid labile ester, and are capable of being developed by an aqueous alkaline solution because the exposed regions turn to the alkaline soluble carboxylic acids. The solubility of the resist composition in an alkaline solution further prevents the swelling of the formed resist pattern after development in contrast with use of an organic solvent as a developer. Thus, using the resist compositions of the invention, it is possible to form fine resist patterns in a short exposure time. Further, it has been discovered that aliphatic polycyclic compounds such as adamantane compounds have high dry etch resistance used in the manufacture of semiconductor devices. The inventive resist compositions exhibit high dry etch resistance, and are very promising chemically amplified resist compositions of a new type.

In the resist compositions of the present invention, any photo acid generator may be used. Photo acid generators contemplated being preferably used in the invention include, but are not limited to, the following:

(1) Triarylsulfonium salts, for example,

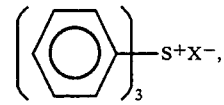

wherein X denotes $PF_6^-$, $AsF_6^-$, $SbF_6^-$, $BF_4^-$, and $CF_3SO_3^-$;

(2) Diaryliodonium salts, for example,

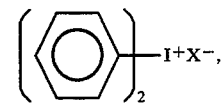

wherein X denotes $PF_6^-$, $AsF_6^-$, $SbF_6^-$, $BF_4^-$, and $CF_3SO_3$;

(3) Sulfonates, for example,

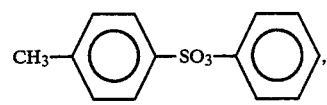

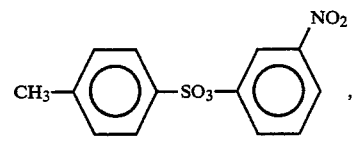

and

-continued

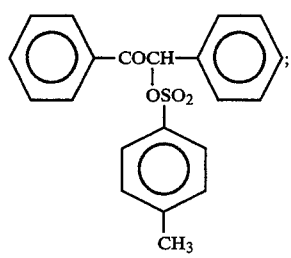

(4) Halides, for example,

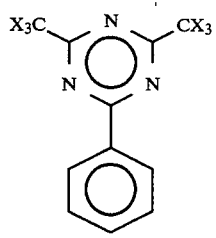

and

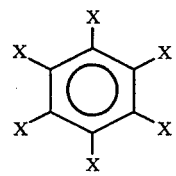

wherein X is Br, Cl, etc.

1-(1,-cyanoethenyl)adamantane used to prepare one of the copolymers of the present invention is a new compound having the following formula:

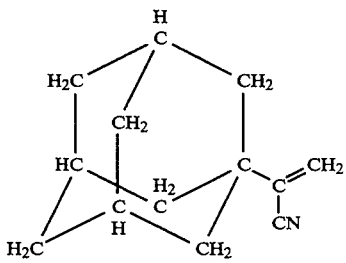

Thus, the adamantane compound of the invention has a cyanoethenyl group in its molecule. This cyanoethenyl group has high polymerization activity unlike the vinyl group and the isopropenyl group in the prior adamantane compounds of 1-vinyl adamantane and 1-isopropenyl adamantane, respectively, and therefore, renders the adamantane compound of the invention copolymerizable with another polymizable monomer to thereby easily provide a desired copolymer. The inventive adamantane compound is preferably copolymerized with an acrylate or methacrylate derivative.

Furthermore, with the inventive 1-(1'-cyanoethenyl)adamantane, reactions may be anticipated which replace a hydrogen atom in the adamantyl group with another atom or group, or which take place at the site of the cyano group. This compound may therefore be commonly used as starting materials for the organic synthesis of polymers, medicines, pesticides or the like.

1-(1'-cyanoethenyl)adamantane of the present invention may be produced utilizing various known processes. For example, as illustrated in the Examples below, the inventor favorably prepared this compound using adamantyl methyl ketone as a starting material, in accordance with the following three step process:

(i) The addition of cyanotrimethylsilane to adamantyl methyl ketone

This addition reaction is shown by the formula:

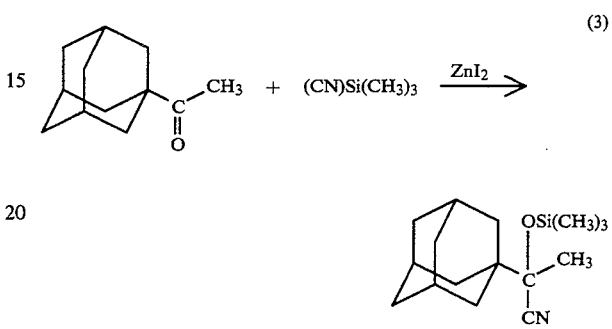

(3)

The reaction may easily be carried out by, for example, addition of cyanotrimethylsilane (TMSCN) to adamantyl methyl ketone in the presence of zinc iodide catalyst, in dry methylene chloride as a solvent and under nitrogen atmosphere, to thereby produce the adduct, i.e., cyanotrimethylsilyl ether, in a high yield. After the completion of the reaction, the solvent is removed, and the residue is then purified to provide the adduct of high purity.

(ii) The hydrolysis of the trimethylsilyl ether

The hydrolysis is represented as follows:

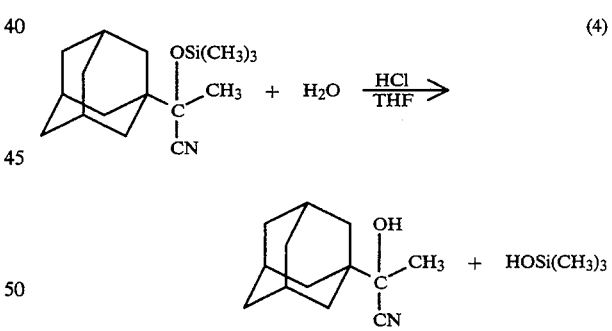

(4)

This hydrolysis reaction of the trimethylsilyl ether may be carried out by, for example, heating it with diluted hydrochloric acid in tetrahydrofuran (THF). After the completion of the reaction, the reaction solution is neutralized by an aqueous alkaline solution, the organic layer is then separated from the aqueous layer, and washed with water and brine. The water layer is then extracted with ether. The ether layer is combined with the former organic layer, dried, and then concentrated under reduced pressure, to thereby provide the corresponding hydroxyl product with ease and in a high yield.

(iii) The dehydration of the hydroxylated product

This reaction is indicated by the formula:

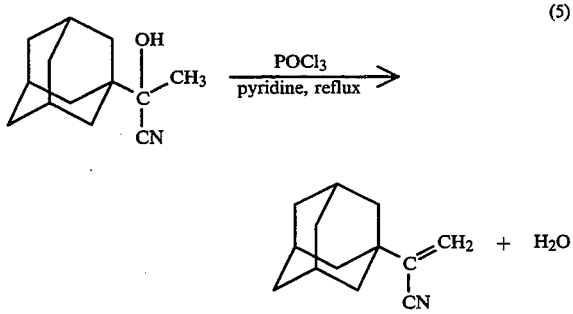

The hydroxylated product is dissolved in pyridine, and an excess amount of phosphorus oxychloride is added and stirred under reflux. After the finish of the reaction, the reaction mixture is stirred at 0° C. and diluted with ether, and ice is then added carefully to hydrolyze the excess phosphorus oxychloride. Subsequently, the resulting solution is extracted several times with ether. The combination of the extracts is washed with a diluted aqueous alkaline solution and brine, and the solvent is removed in vacuo. The residue is purified to yield 1-(1'-cyanoethenyl)adamantane.

The process for preparing 2-norbornene-2-carbonitrile, which is another starting material for the production of the copolymer with an acrylate or methacrylate derivative according to the invention, is known (Brian Byrne et al., Tetrahedron Lett., 2189 (1976)). However, since that synthetic route could not successfully be applied, the inventor synthesized the compound through the synthetic route comprising the reactions shown by the following formulae:

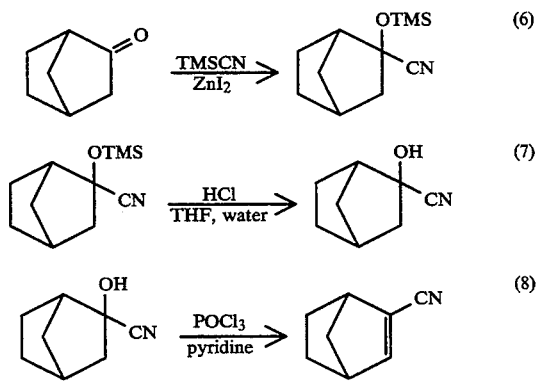

In principle, these reactions are the same as those employed for the above described preparation process for 1-(1'-cyanoethenyl)adamantane, and will be further illustrated in the Examples below.

For a person with ordinary skill in the art to further understand the present invention, the following Examples are presented. It should be noted that the Examples are provided for the illustration only, and are not to be interpreted to limit the invention.

EXAMPLE 1

This Example demonstrates the production of 1-(1'-cyanoethenyl)adamantane.

(i) Preparation of 1-(1'-cyano-1'-trimethylsiloxyethyl)adamantane

To a well dried, 100 milliliter three-necked flask provided with a rubber septum, a calcium chloride tube, and a Dimroth condenser, and containing a stirrer bar coated with polytetrafluoroethylene (PTFE), 17.115 grams (96 millimoles) of adamantyl methyl ketone, 500 milligrams of zinc iodide, and 20 milliliters of anhydrous methylene chloride were added. The mixture was then stirred under nitrogen atmosphere at 10° C. To this mixture, 10 grams (100.8 millimoles) of cyanotrimethylsilane (TMSCN) was introduced dropwise using a cannula of PTFE tube. After one hour stirring, the reaction mixture was allowed to warm to room temperature, and the solution was stirred for additional 4 hours. After the confirmation of the completion of reaction by a thin-layer chromatography, the solvent was removed in vacuo, the residue was then purified by a silica gel column chromatography. Successive elution with 2 and 4% ethyl acetate/hexane gave 1-(1'-cyano-1'-trimethylsiloxyethyl)adamantane as white crystals, and the yield was 26.4 grams (quantitative). By the infrared spectrophotometry of the compound, the following result (KBr, disc, cm$^{-1}$) was obtained:

2905, 2659 (vw), 2227 (vw), 1449, 1252, 1127, 1002, 866, 843, 764, 627.

(ii) Preparation of 1-(1'-cyano-1'-hydroxyethyl)adamantane

To a 200 milliliter Erlenmeyer flask containing a PTFE-coated stirrer bar, 9.11 grams (32.9 millimoles) of 1-(1'-cyano-1'-trimethylsiloxyethyl)adamantane, 15 milliliters of tetrahydrofuran, and 15 milliliters of 2N hydrochloric acid was added. The flask was then equipped with a Dimroth condenser, and the mixture was vigorously stirred at 80° C. After ten hour stirring, the disappearance of the starting material was confirmed by a thin-layer chromatography. Subsequently, the reaction solution was cooled to 0° C., and a dilute aqueous potassium hydrogencarbonate solution was slowly added to neutralize, with vigorously agitating.

The oil layer was then separated by a separating funnel. The water layer was extracted three times with diethyl ether, and the extracts were combined. The ethereal solution was washed with brine, and dried with anhydrous sodium sulfate. The sodium sulfate was filtered out, and the solvent was then removed in vacuo, to thereby yield white crystals of the crude product of 1-(1'-cyano-1'-hydroxyethyl)adamantane.

Yield: 6.71 grams (quantitative).

IR (KBr, disc, cm$^{-1}$): 3506, 2909, 2678 (vw), 2226 (w), 1451, 1355, 1134, 919, 819.

Since the presence of by-products was not observed, the prepared compound was used for the subsequent reaction, without purification.

(iii) Production of 1-(1'-cyanoethenyl)adamantane

To a 200 milliliter Erlenmeyer flask containing a PTFE-coated stirrer bar, 8.80 grams (42.9 millimoles) of 1-(1'-cyano-1'-hydroxyethyl)adamantane was added. Subsequently, 60 milliliters of anhydrous pyridine and 11.7 milliliters (129 millimoles) of phosphorus oxychloride were added, and were allowed to reflux with stirring. Ten hours after, the disappearance of the starting material was confirmed by a thin-layer chromatography, and the solution was then allowed to cool to room temperature. The reaction solution was diluted with diethyl ether, and the diluted solution was slowly poured into 200 milliliters of 4N hydrochloric acid and ice at 0° C. with vigorous stirring. Ice was added to maintain the temperature of the solution at 0° C. After the diluted solution was completely added, the stirring was continued for additional 1 hour.

Subsequently, the oil layer was separated, and the water layer was extracted three times with diethyl ether. The extracts were combined, and the resulting mixture was washed with diluted aqueous potassium hydrogencarbonate solution and brine, and dried with anhydrous sodium sulfate. Subsequently, the sodium sulfate was filtered out, the solvent was removed in vacuo. The residue was then purified by a silica gel column chromatography, and the fraction eluted in 4/96 diethyl ether/hexane was collected.

The obtained 1-(1'-cyanoethenyl)adamantane was a colorless, clear liquid. The yield of this product was 7.62 grams (94.8 percent). The results of infrared spectrophotometry (IR) (KBr, neat, cm$^{-1}$), $^1$H NMR and $^{13}$C NMR spectroscopic analyses (CDCL$_3$, δ, TMS as internal standard) are shown below:

IR: 2906, 2680, 2220 (m), 1614, 1452, 931, 927;

$^1$H NMR: 5.81 (1H, singlet), 5.63 (1H, singlet), 2.08 (3H, multiplet), 1.77–1.63 (12H, multipier);

$^{13}$C NMR: 134.1 (s), 126.1 (t), 117.8 (s), 4.05 (t), 36.8 (s), 36.3 (t), 28.1 (d).

Of the IR data, the peak at 2220 cm$^{-1}$ is the result of alpha, beta-unsaturated nitrile in the adamantane compound, and the peak at 1614 cm$^{-1}$ is conjugated double bonds. Of the $^1$H NMR data, the peaks at 5.81 and 5.63 ppm result from the methylene proton in cyanoethenyl group, the peak at 2.08 ppm the methane proton in adamantane skeleton. The peak at 117.8 ppm of the 13C NMR data results from the carbon atom in the cyano group.

EXAMPLE 2

This Example illustrates the synthesis of 2-norbornene-2-carbonitrile.

(i) Preparation of 2-cyano-2-trimethylsiloxy-norbane

To a well dried, 200 milliliter three-necked flask equipped with a rubber septum, a calcium chloride tube, and a Dimroth condenser, and containing a PTFE-coated stirrer bar, 20.19 grams (183.3 millimoles) of 2-norbornanone, 1 gram of zinc iodide, and 50 milliliters of anhydrous methylene chloride were added. The mixture was then stirred under nitrogen atmosphere at −20° C. To this solution, 20 grams (201.6 millimoles) of TMSCN was introduced dropwise using a cannula of PTFE tube. Two hours later, the solution was allowed to warm to room temperature, and the reaction solution was stirred for 6 hours. After confirmation of the completion of reaction by a thin-layer chromatography, the solvent was removed under reduced pressure. The residue was then purified by a silica get column chromatography, to thereby provide 2-cyano-2-trimethylsiloxynorbornane (the mixture of end:exo=8:1), which was a light yellow liquid.

Yield: 38.27 grams (quantitative).

IR (KBr, neat, cm$^{-1}$): 2962, 2877 (m), 2229 (w), 1456, 1254, 1176, 1104, 910, 846, 758.

(ii) Preparation of 2-cyano-2-hydroxynorbornane

Into a 200 milliliter Erlenmeyer flask, 38.37 grams (183.3 millimoles) of 2-cyano-2-trimethylsiloxynorbornane obtained in A, a PTFE-coated stirrer bar, 30 milliliters of tetrahydrofuran, 10 milliliters of water, and 1 milliliter of 2N hydrochloric acid were placed. This mixture was vigorously stirred at room temperature. Three hours later, the disappearance of the starting norbornane compound was confirmed by thin-layer chromatography, and 1 milliliter of 2N aqueous potassium hydrogencarbonate solution was then added to the reaction mixture and the mixture was vigorously stirred for 5 minutes. The reaction mixture was poured into water and extracted three times with diethyl ether, and the extracts were combined, washed with brine, and dried with anhydrous sodium sulfate. The sodium sulfate was then filtered out. The solvent was subsequently removed in vacuo to thereby yield a crude product. Distillation of the crude product under reduced pressure gave 2-cyano-2-hydroxynorbornane (exo/endo mixture) as a colorless, clear liquid having a boiling point of 85.5°–86.0° C. (0.35 mmHg).

Yield: 21.41 grams (84.5%).

IR (KBr, neat, cm$^{-1}$): 3420 (s), 2962, 2877, 2238 (m), 1455, 1312, 1173, 1074 (s), 819, 981.

(iii) Production of 2-norbornene-2-carbonitrile

Into a dry, 200 milliliter Erlenmeyer flask, 7.12 grams (51.5 millimoles) of 2-cyano-2-hydroxynorbornane obtained in (ii), and a PTFE-coated stirrer bar were placed. The flask was then fully purged with nitrogen, and 60 milliliters of anhydrous pyridine and 14.1 milliliters (155 millimoles) of phosphorus oxychloride were added. The mixed solution was then stirred under reflux. Ten hours later, the disappearance of the starting compound was confirmed by thin-layer chromatography, and the solution was allowed to cool to room temperature. The reaction mixture was then diluted with diethyl ether to a volume of 200 milliliters, and the diluted solution was slowly poured into 200 milliliters of agitated 4N hydrochloric acid and ice at 0° C. with vigorous stirring. Ice was added to maintain the temperature of the solution at 0° C. After the diluted solution was totally added, the stirring was further continued for 1 hour.

Subsequently, using a separating funnel, the oil layer was separated, and the water layer was then extracted three times with ether. The extracts were combined and washed with a diluted aqueous potassium hydrogencarbonate solution and brine, and dried with anhydrous sodium sulfate. The sodium sulfate was then filtered out, the solvent was removed in vacuo, and the resultant residue was subjected to vacuum distillation, to yield 2-norbornene-2-carbonitrile (84% purity) as a colorless, clear liquid, bp 57°–58° C. (4–5 mmHg).

Yield: 4.21 grams (68.0%).

IR (KBr, neat, cm$^{-1}$): 2973, 2876, 2215 (s), 1580 (m), 1447 (m), 1314, 879, 603.

$^1$H NMR (CDCL$_3$, δ, TMS as internal standard): 6.89 (1H, d, J=3.2 Hz), 3.15 (1H, s), 3.07 (1H, m), 1.9–1.63 (2H, m), 1.62–1.47 (1H, m), 1.32–1.03 (3H, m).

$^{13}$C NMR (CDCL$_3$, δ): 152.7 (d), 118.9 (s), 116.5 (s), 48.5 (t), 45.3 (d), 43.3 (d), 24.2 (t), 24.0 (t).

EXAMPLE 3

Various copolymers of 1-(1'-cyanoethenyl)adamantane with a methacrylate derivative were synthesized, as follows:

A. Copolymer of 1-(1'-cyanoethenyl)adamantane with methyl methacrylate

Into a 50 milliliter three-necked flask provided with a nitrogen introducing tube, a calcium chloride tube, a Dimroth condenser, and a PTFE-coated stirrer bar, 5 grams (26.7 millimoles) of 1-(1'-cyanoethenyl)adamantane, and 2.67 grams (26.7 millimoles) of methyl methacrylate were added, and nitrogen was bubbled up through the solution in the flask for 20 minutes. Then, 175 milligrams (1.06 millimoles) of azobisisobutyronitrile was added to the solution, and stirred at 75° C. while slowly introducing nitrogen. Twelve hours later, the reaction solution was dropped into 1 liter of hexane containing a small amount of hydroquinone, and the resultant precipitate was filtered out by a glass filter. The filtered precipitate was dried at 50° C. and 0.5 mmHg for 6 hours. The resultant powder was dissolved in tetrahydrofuran, and subjected again to the precipitation and drying as described above. The freshly obtained powder was further dissolved, precipitated, and dried at 50° C. and 0.5 mmHg for 12 hours, to thereby produce 566 milligrams of copolymer (7.4% yield) as white powder which was characterized by the following particulars:

Composition ratio: adamantane:methacrylate = 10:90;
Weight-average molecular weight (Mw): 3,100;
Polydispersity index (Mw/Mn): 1.22;
IR (KRS-5, cm$^{-1}$): 2993, 2951, 2233 (vw), 1733 (s), 1484, 1450, 1242, 1193, 1150, 989 (m), 751 (w).

In the IR data, the abbreviations s, m, w, and vw mean strong, medium, weak, and very weak, respectively.

B. Copolymer with tert-butyl methacrylate

To a well dried, 100 milliliter three-necked flask equipped with a nitrogen introducing tube, a calcium chloride tube, and a rubber septum, and containing a PTFE-coated stirrer bar, 8.70 grams (46.4 millimoles) of 1-(1'-cyanoethenyl)adamantane, 4.4 grams (30.9 millimoles) of tert-butyl methacrylate, 347 milligrams (3.1 millimoles) of potassium tertbutoxide, and 15.5 milliliters of tetrahydrofuran were added, and the mixture was stirred at 0° C. under a nitrogen atmosphere. 3.1 milliliters (3.1 millimoles) of 1M tetrahydrofuran solution of 18-crown-6 was slowly added, and the resultant solution was then stirred at 0° C. for 2 hours and subsequently at room temperature for 17 hours. The reaction was terminated by adding 10 milliliters of a commercial grade of tetrahydrofuran. Thereafter, the reaction solution was dropped into 1.5 liters of methanol, and the resultant precipitate was filtered out by a glass filter, and was dried at 50° C. and 0.2 mmHg for 6 hours. The obtained powder was dissolved in tetrahydrofuran, and subjected again to the precipitation, filtration and drying as described above, to thereby obtain the fresh powder. This powder was further dissolved in tetrahydrofuran, and was subsequently subjected to the precipitation, filtration, and drying at 50° C. and 0.2 mmHg for 12 hours, to thereby produce 2.93 grams of copolymer (22.4% yield) as white powder which was characterized by the following particulars:

Composition ratio: adamantane:methacrylate = 20:80;
Mw: 17,000;
Polydispersity index (Mw/Mn): 1.50;
IR (KRS-5, cm$^{-1}$): 2976, 2932, 2909, 2853, 2231 (w), 1723, 1477, 1456, 1393, 1368, 1253, 1140, 849.

C. Copolymer with tetrahydropyranyl methacrylate

To a well dried, 100 milliliter three-necked flask equipped with a nitrogen introducing tube, a calcium tube, and a rubber septum, and containing a PTFE coated stirrer bar, 8.00 grams (42.7 millimoles) of 1-(1'-cyanoethenyl)adamantane, 4.85 grams (28.5 millimoles) of tetrahydropyranyl methacrylate, 3.6 milliliters (3.6 millimoles) of 1M potassium tertbutoxide/tetrahydrofuran solution, and 14.2 milliliters of tetrahydrofuran were added, and the mixture was stirred at 0° C. under a nitrogen atmosphere. 3.6 milliliters (3.6 millimoles) of 1M tetrahydrofuran solution of 18-crown-6 was slowly added, and the resultant solution was then stirred at 0° C. for 1 hour and subsequently at room temperature for 17 hours. The reaction was terminated by adding 10 milliliters of a commercial grade of tetrahydrofuran. Thereafter, the reaction solution was dropped into a mixed solution of 900 milliliters of hexane and 100 milliliters of diethyl ether, and the resultant precipitate was filtered out by a glass filter, and was dried at 50° C. and 0.2 mmHg for 6 hours. The obtained powder was dissolved in tetrahydrofuran, and subjected again to the precipitation, filtration and drying as described above, to thereby obtain the fresh powder. This powder was further dissolved in tetrahydrofuran, and was subsequently subjected to precipitation, filtration, and drying at 50° C. and 0.2 mmHg for 16 hours, to thereby produce 2.78 grams of copolymer (21.6% yield) as white powder which was characterized by the following particulars:

Composition ratio: adamantane:methacrylate = 31:69;
Mw: 12,000;
Polydispersity index (Mw/Mn): 1.25;
IR (KRS-5 cm$^{-1}$): 2942, 2233 (vw), 1730, 1554, 1455, 1388, 1358, 1168, 1113, 1037, 943, 901, 870, 598 (m).

EXAMPLE 4

Two types of copolymer of 2-norbornene-2-carbonitrile with a methacrylate derivative were produced, as follows:

A. Copolymer of 2-norbornene-2-carbonitrile with tetrahydropyranyl methacrylate Into a well dried, 100 milliliter three-necked flask as used in Example 3, a PTFE-coated stirrer bar, 5 grams (41.6 millimoles) of 2-norbornene-2-carbonitrile, 4.72 grams (27.7 millimoles) of tetrahydropyranyl methacrylate, and 13.9 milliliters of anhydrous tetrahydrofuran (THF) were placed, and the mixture was then stirred at −17° C. under nitrogen atmosphere for 10 minutes. To this solution, 311 milligrams (2.8 millimoles) of potassium tert-butoxide dissolved in 4 milliliters of dry THF was slowly dropped via a syringe. Then, 740 milligrams (2.8 millimoles) of 18-crown-6 dissolved in 2 milliliters of THF was slowly dropped into the reaction solution via a syringe to maintain the temperature of the reaction mixture, and the reaction mixture was stirred for 1.5 hours. The temperature of the reaction mixture was then allowed to warm to room temperature, and the solution was stirred for an additional 4 hours. The reaction was terminated by adding 10 milliliters of a commercial grade of THF. The reaction solution was then dropped into 1.5 liters methanol. The resultant precipitate was filtered out by a glass filter, and was dried at 40° C. and 0.5 mmHg for 6 hours. The white powder thus obtained was redissolved in 30 milliliters of THF, and further subjected again to the precipitation, filtration and drying as described above. The dried white powder was further subjected to the dissolution, precipitation, filtration, followed by drying at 40° C. and 0.5 mmHg for 16 hours. The finally obtained copolymer (3.85 grams, 34.5% yield) which was soluble in tetrahydrofuran and methylene chloride and insoluble in methanol and hexane, was characterized by the following particulars:

Composition ratio: norbornane:methacrylate = 36:64 (by NMR);
Mw: 32,000;
Mw/Mn: 1.73;
IR (KRS-5, film, cm$^{-1}$): 2945, 2878, 2229 (w), 1733, 1455, 1112, 1037, 900, 868, 821.

B. Copolymer with tert-butyl methacrylate

Into a well dried, 100 milliliter three-necked flask as used in Example 3, a PTFE-coated stirrer bar, 7.5 grams (62.4 millimoles) of 2-norbornene-2-carbonitrile, 5.91 grams (41.6 millimoles) of tert-butyl methacrylate, and 20.8 milliliters of anhydrous THF were placed, and the mixture was then stirred at $-17°$ C. under a nitrogen atmosphere for 10 minutes. To this solution, 467 milligrams (4.2 millimoles) of potassium tertbutoxide dissolved in 5 milliliters of anhydrous THF was slowly dropped via a syringe to maintain the temperature of the reaction mixture. The reaction mixture was stirred at $-17°$ C. for 30 minutes, and the reaction was terminated by adding 50 milliliters of a commercial grade of THF. The reaction solution was then dropped into 2 liters of methanol, and the resultant precipitate was filtered out by a glass filter, and was dried at 60° C. and 0.5 mmHg for 6 hours. The pale yellow powder thus obtained was redissolved in 100 milliliters of THF, and further subjected again to precipitation, filtration and drying as described above. The dried, pale yellow powder was further subjected to the dissolution, precipitation, filtration, followed by drying at 60° C. and 0.5 mmHg for 16 hours. The finally obtained copolymer (5.75 grams, 42.9% yield) which was soluble in chlorobenzene and methylene chloride and insoluble in methanol, hexane and diethyl ether, was characterized by the following particulars:

Composition ratio: norbornane:methacrylate=59:41; (by elemental analysis)
Elemental analysis:
C 73.18%
H 8.47%
N 6.46%
Mw: 17,000;
Mw/Mn: 1.57;
IR (KRS-5, film, cm$^{-1}$): 2975, 2937, 2881, 2229 (w), 1721, 1460, 1369, 1252, 1138 (s), 848.

EXAMPLE 5

The resist composition of this Example comprised the copolymer of 1-(1'-cyanoethenyl)adamantane with tetrahydropyranyl methacrylate produced in Example 3C and an photo acid generator. The transmittance data of this copolymer at KrF wavelength (248 nm) and ArF wavelength (193 nm) were 90% and 65%, respectively. The UV spectrum of the copolymer was measured using a 1 micrometer thickness film of the copolymer, which was formed by spin-coating the copolymer solution onto a synthetic quartz substrate.

The copolymer was dissolved in cyclohaxanone to make a solution having a concentration of 15% by weight. To this solution, 15% by weight (based on the weight of the copolymer) of triphenylsulfonium hexafluoroantimonate was added, to provide a resist composition.

This resist composition was spin-coated onto an SiO$_2$ substrate which had been treated with hexamethyldisilazane (HMDS), and was baked at 60° C. for 20 minutes in oven, to thereby form a 0.6 micrometer thickness film. The film was then exposed with a KrF excimer laser stepper (NA=0.45). Subsequently, the film was baked at 100° C. for 60 seconds on a hot plate, and a given resist pattern was developed in dipmode using a 2.38% aqueous tetramethylammonium hydroxide (TMAH) solution to give a resist pattern. A 0.5 micrometer line-and-space patterns were resolved at a dose of 10 mJ/cm$^2$. The etching resistance was investigated using the formed resist pattern as a mask. The substrate was etched by a mixed gas of CF$_4$ and O$_2$ (CF$_4$/O$_2$=0.95/0.05), at 0.3 torr and 300 watts. The resist film showed a good dry etching resistance, which was comparable to that of Nagase positive resist 820 supplied by Nagase Sangyo, Japan.

EXAMPLE 6

The resist composition of this Example comprised the copolymer of 2-norbornene-2-carbonitrile with tetrahydropyranyl methacrylate produced as in Example 4B and a photo acid generator. The transmittance data of this copolymer at KrF wavelength (248 nm) and ArF wavelength (193 nm) were 90% and 60%, respectively. The UV spectrum of the copolymer were measured as described in Example 5.

Repeating the same procedure as that shown in Example 5, a 0.5 micrometer line-and-space resist patterns were resolved at a dose of 8 mJ/cm$^2$. The etching resistance investigation was carried out as in Example 5, and it was found that the resistance was comparable to that of Nagase positive resist 820.

As can be seen from the above Examples, 1-(1'-cyanoethenyl)adamantane of the invention as well as the copolymers of 1-(1'-cyanoethenyl)adamantane or 2-norbornene-2-carbonitrile with an acrylate or methacrylate derivative of the invention can easily be produced by the illustrated processes. The processes for synthesizing these novel compounds and copolymers are, however, not limited to those described herein. It would be apparent to a person with ordinary skill in the art that the compound and copolymers of the present invention could be produced by different other processes in which various synthesis methods are applied.

The inventive 1-(1'-cyanoethenyl)adamantane has a polymerizable cyanoethenyl group in its molecule. Moreover, reactions may be expected to occur which replace a hydrogen atom at the bridge head in the adamantyl group with another atom or functional group, or which take place at the site of cyano group. Thus, this new adamantane compound has possible utility for a starting material for syntheses of various organic materials, including polymers, and pharmaceutical and agricultural chemicals.

The compound can advantageously used as a synthesizing material for a functional polymer material, and when used as such a material, i.e., a polymerizable monomer, the compound would provide the highest feasibility. The inventive 1-(1-cyanoethenyl)adamantane may provide a copolymer through a reaction with another copolymerizable monomer in the presence of, e.g., an anion catalyst, such as a metal alkoxide, metal alkyl or Grignard reagent, or a radical generator. Copolymers having improved properties may be obtained by selecting a suitable copolymerizable monomer to be copolymerized with the adamantane monomer depending on the use and purposes of the copolymer.

Although known adamantane compounds, such as 1-vinyladamantane and 1-isopropenyladamantane, provide homopolymers by a cation catalyst, none of these compounds can provide a copolymer with an acrylate or methacrylate monomer by such a cation catalyst, which makes it difficult to attempt the modification of polymer. Thus, the polymers based on the prior adamantane compounds have only limited applicability. Unlike the prior compounds, the inventive 1-(1'-cyanoethenyl)adamantane makes it possible to provide desired polymers which are designed to adapt to given uses and purposes, and may present extended applicability.

The copolymers according to the present invention are novel, and may be expected to show unique characteristics which are not obtained by conventional materials. The copolymers would therefore be applied to various fields exemplified above.

Known copolymers having a unit resulting from an adamantane or norbornene based monomer as one of structural units, such as referred to hereinbefore, inherently have faults such as high hardness and high absorbency in the far ultraviolet region. In contrast, the copolymers of the present invention are superior in transparency, and attain moderate softness to thereby provide improved processability, by virtue of the incorporation of structural units based on a monomer such as methacrylate derivative. More specifically, the copolymers of the invention combined with a suitable photo acid generator provide excellent resist compositions which are capable of forming thinner resist film and providing finer resist patterns required in the manufacture of advanced, highly integrated semiconductor devices.

I claim:

1. A resist composition comprising a polymer material and an acid generator, wherein the polymer is a copolymer of 1-(1'-cyanoethenyl)adamantane with an acrylate or methacrylate derivative having the following formula:

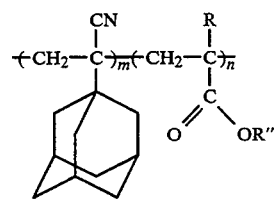

wherein R is hydrogen or methyl group;
R'' is a tert-butyl group or tetrahydropyranyl group; and
m and n are integers greater than zero.

2. The composition of claim 1, wherein the ratio of m to n is 30:70 to 70:30.

3. The composition of claim 1, which has an average molecular weight of 2,000 to 1,000,000.

4. The composition of claim 1, wherein the acid generator is present in an amount of 1 to 50% by weight based on the weight of the copolymer.

5. The composition of claim 4, wherein the acid generator is selected from the group consisting of triarylsulfonium salts, diaryliodonium salts, sulfonates, and halides.

* * * * *

UNITED STATES PATENT AND TRADEMARK OFFICE
CERTIFICATE OF CORRECTION

PATENT NO. : 5,399,647
DATED : March 21, 1995
INVENTOR(S) : KOJI NOZAKI

It is certified that error appears in the above-indentified patent and that said Letters Patent is hereby corrected as shown below:

Column 11, line 19, delete "(12H, multipier)" and substitute --(12H, multiplet)--;

Column 11, line 27, delete "methane" and substitute --methyne--;

Column 11, line 28, delete "13C" and substitute --$^{13}$C--;

Column 11, line 50, delete "get" and substitute --gel--.

Signed and Sealed this

Thirtieth Day of May, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,399,647
DATED : March 21, 1995
INVENTOR(S) : KOJI NOZAKI

It is certified that error appears in the above-indentified patent and that said Letters Patent is hereby corrected as shown below:

Title Page [62] Related U.S. Application Data, delete "Pat. No. 5,342,735" and substitute --now abandoned--.

Signed and Sealed this

First Day of August, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,399,647
DATED : March 21, 1995
INVENTOR(S) : KOJI NOZAKI

It is certified that error appears in the above-indentified patent and that said Letters Patent is hereby corrected as shown below:

Title Page [56] under References Cited insert:

-- OTHER DOCUMENTS

Vysokomol. Soed 22(1980) Ser. B, No. 1, pp. 3-4;

ref. in Hochmolekularbericht 11384/80 --

Signed and Sealed this

Sixteenth Day of July, 1996

Attest:

BRUCE LEHMAN

Attesting Officer        Commissioner of Patents and Trademarks